(12) United States Patent
Yamamoto (10) Patent No.: US 11,430,038 B2
(45) Date of Patent: Aug. 30, 2022

(54) MENU DISPLAY METHOD, MENU DISPLAY DEVICE, AND MENU DISPLAY PROGRAM (71) Applicant: Mako Enterprise Co., Ltd., Nagano (JP)

(72) Inventor: Takashi Yamamoto, Shimotakai-gun (JP)

(73) Assignee: MAKO ENTERPRISE CO., LTD., Nagano (JP)

( * ) Notice: Subject to any disclaimer, the term of this patent is extended or adjusted under 35 U.S.C. 154(b) by 428 days.

(21) Appl. No.: 16/500,309

(22) PCT Filed: Jul. 3, 2018

(86) PCT No.: PCT/JP2018/025129
§ 371 (c)(1),
(2) Date: Oct. 2, 2019

(87) PCT Pub. No.: WO2019/044159
PCT Pub. Date: Mar. 7, 2019

(65) Prior Publication Data
US 2021/0097592 A1   Apr. 1, 2021

(30) Foreign Application Priority Data
Sep. 4, 2017   (JP) .............................. JP2017-169413

(51) Int. Cl.
G06F 3/0482   (2013.01)
G06Q 30/06   (2012.01)
(Continued)

(52) U.S. Cl.
CPC ....... *G06Q 30/0627* (2013.01); *G06F 3/0482* (2013.01); *G06F 16/248* (2019.01);
(Continued)

(58) Field of Classification Search
CPC ................................................. G06Q 30/0627
See application file for complete search history.

(56) References Cited

U.S. PATENT DOCUMENTS

| 5,899,502 A * | 5/1999 | Del Giorno ............ G06Q 99/00 |
| | | 283/67 |
| 6,859,215 B1 * | 2/2005 | Brown .................... G06Q 30/06 |
| | | 705/26.5 |

(Continued)

FOREIGN PATENT DOCUMENTS

| JP | 9-26952 A | 1/1997 |
| JP | 2000-99578 A | 4/2000 |

(Continued)

OTHER PUBLICATIONS

International Search Report (PCT/ISA/210) issued in PCT/JP2018/025129, dated Sep. 25, 2018.

*Primary Examiner* — Anil K Bhargava
(74) *Attorney, Agent, or Firm* — Birch, Stewart, Kolasch & Birch, LLP (57) ABSTRACT

To provide a menu display method capable of preventing a check error while rationalizing the work of checking information of ingredients to avoid of dishes in plural menus with information of ingredients to avoid of users by performing computer processing, and further capable of clarifying which dish is to be changed from a changed menu table. As a solution, menu display procedures of the menu display method include Step S1 of extracting data, Step 2 of checking information of ingredients to avoid, Step S3 of determining whether first information of ingredients to avoid overlaps with second information of ingredients to avoid or not, Step S4 of searching a first dish name when the information of ingredients to avoid overlaps, Step S5 of determining whether the first dish name exists in basic menu table information or not, Step S6 of extracting a second dish (Continued)

name, Step S7 of giving a prohibition display to the first dish name, Step S8 of arranging the second dish name and Step S9 of outputting individual menu table information.

6 Claims, 6 Drawing Sheets

(51) Int. Cl.
*G16H 20/60* (2018.01)
*G06F 16/2457* (2019.01)
*G06F 16/248* (2019.01)
*G06Q 50/12* (2012.01)
*G06F 3/0488* (2022.01)

(52) U.S. Cl.
CPC ....... *G06F 16/24578* (2019.01); *G06Q 50/12* (2013.01); *G16H 20/60* (2018.01); *G06F 3/0488* (2013.01)

(56) References Cited

U.S. PATENT DOCUMENTS

| | | | | |
|---|---|---|---|---|
| 2003/0158465 A1* | 8/2003 | Galli | ............... | G16H 20/60 600/300 |
| 2011/0071865 A1* | 3/2011 | Leeds | ............... | G06Q 10/025 707/E17.014 |
| 2014/0173602 A1* | 6/2014 | Kikin-Gil | ......... | G06Q 10/1097 718/100 |
| 2014/0279087 A1* | 9/2014 | Hurst | ............... | G06Q 50/12 705/15 |
| 2015/0079551 A1* | 3/2015 | Egan | ............... | G09B 19/0092 434/127 |
| 2017/0098267 A1* | 4/2017 | Hokazono | ......... | G06Q 30/0627 |
| 2017/0109350 A1* | 4/2017 | Nagano | ............... | G06F 16/51 |
| 2018/0233064 A1* | 8/2018 | Dunn | ............... | G09B 19/0092 |
| 2018/0268503 A1* | 9/2018 | Parikh | ............... | G06Q 30/0627 |
| 2020/0043614 A1* | 2/2020 | Washida | ............... | G16H 10/60 |

FOREIGN PATENT DOCUMENTS

| | | |
|---|---|---|
| JP | 2003-216738 A | 7/2003 |
| JP | 2005-18181 A | 1/2005 |
| JP | 2008-27148 A | 2/2008 |
| JP | 2008-217610 A | 9/2008 |
| JP | 5034564 B2 | 9/2012 |
| JP | 2016-38869 A | 3/2016 |
| JP | 2017-76351 A | 4/2017 |

* cited by examiner

| | BREAKFAST | LUNCH | DINNER |
|---|---|---|---|
| 1st SEP | | | BEEF DICED STEAK MABO TOFU<br><br>MACARONI SALAD<br><br>PUMPKIN SOUP CAKE |
| 2nd SEP | OMELETTE<br><br>SALT-GRILLED MACKEREL<br><br>SPINACH WITH SESAME SEEDS<br><br>PEACH AND PEAR<br><br>RICE AND MISO SOUP | BEEF BOWL<br><br>ORANGE JELLY<br><br>MISO SOUP | |

GROUP NAME: PQR

FIG.4

| DISH SEGMENT | PRIORITY | DISH NAME | EGG | MILK | WHEAT | | PORK |
|---|---|---|---|---|---|---|---|
| A | 1 | BEEF DICED STEAK | | | ○ | | |
| | 2 | PORK SHABU-SHABU | | | | | ○ |
| | 3 | ROASTED SEAFOOD ON CERAMIC PLATE | | | | | |
| B | 1 | MABO TOFU | | | ○ | | ○ |
| | 2 | SHRIMPS WITH CHILI SOURCE | | | ○ | | |
| | 3 | OVEN-BAKED WHITE FISH | ○ | | | | |
| C | 1 | MACARONI SALAD | ○ | | ○ | | |
| | 2 | GREEN SALAD | | | | | |
| | 3 | WARM VEGETABLES | | | | | |
| D | 1 | PUMPKIN SOUP | | ○ | ○ | | |
| | 2 | CORN SOUP | | ○ | ○ | | |
| | 3 | CHINESE SOUP | | | | | |
| E | 1 | CAKE | ○ | ○ | ○ | | |
| | 2 | FRUIT | | | | | |
| | 3 | YOGURT | | ○ | | | |

FIG.5

| GROUP NAME | INDIVIDUAL NAME | EGG | MILK | WHEAT | PORK |
|---|---|---|---|---|---|
| PQR | abc01 | | | | |
| | abc02 | ○ | | | |
| | abc03 | | | | |
| | abc04 | ○ | | ○ | |
| | abc05 | | | | |
| | abc06 | | | | |
| | abc07 | | | | |
| | abc08 | | ○ | | |
| | abc09 | | | | |
| STU | def01 | | | | |
| | def02 | | | | |
| | def03 | ○ | | | |
| | def04 | | | | |
| | def05 | | | | ○ |
| | def06 | | | | |

FIG.6

| | BREAKFAST | LUNCH | DINNER |
|---|---|---|---|
| 1st SEP | | | BEEF DICED STEAK<br>MABO TOFU<br>~~MACARONI SALAD~~ GREEN SALAD<br>PUMPKIN SOUP<br>~~CAKE~~ FRUIT |
| 2nd SEP | ~~OMELETTE~~<br>FRIED TOFU WITH SOUP<br>SALT-GRILLED MACKEREL<br>SPINACH WITH SESAME SEEDS<br>PEACH AND PEAR<br>RICE AND MISO SOUP | BEEF BOWL<br>ORANGE JELLY<br>MISO SOUP | |

GROUP NAME: PQR
INDIVIDUAL NAME: abc02

MENU DISPLAY METHOD, MENU DISPLAY DEVICE, AND MENU DISPLAY PROGRAM

TECHNICAL FIELD

The present invention relates to a menu display method, a menu display device, and a menu display program.

BACKGROUND ART

In recent years, the number of people having "food allergy" caused by ingestion of food is increasing. The food allergy is a phenomenon in which symptoms disadvantageous to a living body are induced through an antigen-specific immunological mechanism caused by food. There is a case where anaphylactic shock that requires emergency treatment occurs in the food allergy.

There is no obligation of indication prescribed in Food Sanitation Act including allergy indication with respect to dishes served in dining-out places such as restaurants, hotels and inns. However, it is important to enhance the provision of information with respect to people having food-allergic diseases also in the dining-out places to prevent health damage.

In hotels, inns and so on, dishes are normally served to groups a plural number of times. Groups include a family, companions, children, students, workers, corporation employees, a young men's association, a manhood-age group, a women's association, an elderly group, a package tour group arranged by a travel agency, a group of a school excursion, a political organization, a religious group, and other groups. In the specification, the group means two or more people to whom dishes are served.

In a related-art menu planning method by a menu planning device including a processor that executes processing of planning menus for the plural number of times containing one or plural dishes and outputting menu groups indicating the planned menus for the plural number of times for providing plural people with the same menu of dishes in school lunches and so on, there is proposed a method executed by the processor of the menu planning device, which includes a step of deriving a menu group in which respective dishes contained in respective dishes forming menu groups of an original plan are substituted by preset substituted dishes based on the original plan of menu groups showing menus for the plural number of times, a step of counting the number of times of menus not containing ingredients to be allergens for each person to be served by using an ingredient table previously storing ingredients used for dishes in respective menu groups and an allergen table previously storing ingredients to be allergens concerning respective people to whom dishes are served, a step of deriving the minimum value of the number of times counted for each person to be served concerning respective menu groups and a step of determining a menu group to be outputted based on the derived minimum value of the number of times (refer to PTL 1: Japanese Patent No. 5034564)

There is also provided a system including a database for managing personal information including individual constitution information, a database for managing menus of a restaurant and a database for managing ingredient information used for menus in a restaurant of a local government or a company cafeteria, which has a function of confirming personal information, a function of acquiring allergen information associated with personal identification information, a function of determining a menu using an ingredient containing an allergen based on information of the database for managing menus and the database for managing ingredient information used for menus and a function of transmitting a determined result to a terminal in a server device (refer to PTL 2: JP-A-2005-018181).

There is further provided an order registration processing system displaying a warning on a display unit of a customer terminal when a customer determines that an allergen about which the customer should be cautious is contained in the received allergen when the customer orders items by himself/herself by using a tablet terminal in a restaurant (refer to PTL 3: JP-A-2016-038869).

CITATION LIST

Patent Literature

PTL 1: Japanese Patent No. 5034564
PTL 2: JP-A-2005-018181
PTL 3: JP-A-2016-038869

SUMMARY OF INVENTION

Technical Problem

The method described in PTL 1 presupposes that dishes in a uniform menu are served to all members in the so-called school lunches, and it is not supposed to provide people having food allergy and people not having food allergy with different dishes. The method described in PTL 2 displays a decision on a terminal when it is determined that the allergen corresponding to allergy information of a member is contained in the menu before the member places an order to a restaurant, and an irregular response such as replacing one dish in the menu on the restaurant's side when the member orders a dish containing the corresponding allergen is not considered. The same applies to the method of PTL 3.

In hotels, inns and so on in tourist spots, dishes are usually served to groups a plural number of times. In a group of school excursion as an example, people having food allergy exist at a certain percentage. A basic menu table in which plural menus are associated with dates and meal segments is created in inns and so on. Ingredients containing allergens and ingredients not containing allergens are mixed in menus in many cases. As ingredients not containing allergens are limited, it is unrealistic that separate menus are prepared to people having food allergy and people not having food allergy so that menus themselves are not overlapped. Accordingly, food allergy information for respective individuals constituting the group is received from a responsible person of a group of the school excursion or the like in hotels, inns and so on in tourist spots to change part of dishes in menus in people having food allergy and people not having food allergy, that is, menus in which part of dishes are changed will be served to people having food allergy.

In the case where part of dishes in menus are changed, a menu table obtained after change will be one in which part of contents of the menu table created before change is rewritten in a related-art technique. An employee of the inn checks that dishes in plural menus in the changed menu table reflect food allergy information of respective individuals constituting the group of the school excursion or the like with great care. However, a work of checking allergen information of dishes in plural menus with allergen information of plural customers by a human is complicated, and it is difficult to prevent a check error in the check work by the human. Additionally, change history to the changed menu table is unknown, therefore, people serving dishes and people to whom dishes are served suspect that there is any defect such that part of dish names is missing in the changed menu table. That is, the allergen ingredient or a name of a dish containing the corresponding allergen ingredient is deleted and rewritten to a name of a substituted dish or a space is left blank in related art, therefore, there is a problem that which dish is to be changed is unknown from the changed menu table.

International exchange becomes lively in recent years, and borderlessness is accelerating also in regional cities. Various races exist in the world and respective users of dining-out places such as restaurant, hotels and inns may have religious reasons, reasons of diseases and taste or the like in addition to food allergy. Accordingly, it is desirable that dishes served in dining-out places such as restaurant, hotels and inns are made of ingredients corresponding to a vegetarian diet, a Muslim diet (halal processed ingredients), a Judaist diet, a gastrointestinal disease diet (digestible ingredients) and other known ingredients responding to health reasons in addition to an allergen diet. In the specification, ingredients corresponding to allergens, ingredients corresponding to vegetarians, halal-processed ingredients, digestible ingredients and other ingredients responding to health reasons are defined as ingredients to avoid. Also in the specification, users of dining-out places such as restaurant, hotels and inns indicate people or groups to whom dishes are served.

Solution to Problem

The present invention has been accomplished in view of the above circumstances, and an object thereof is to provide a menu display method, a menu display device, and a menu display program capable of preventing a check error while rationalizing the work of checking information of ingredients to avoid of dishes in plural menus with information of ingredients to avoid of users by performing computer processing, and further capable of clarifying which dish is to be changed from a changed menu table.

The above problem will be solved by a solution disclosed below as an embodiment.

A menu display method according to the present invention includes the steps of inputting basic menu table information in which menus are associated with a user name and meal segments, dish table information in which dish names forming the menus are respectively associated with dish segments and first information of ingredients to avoid, and priorities are given in the dish segment, and individual table information in which individual names forming the user name are associated with second information of ingredients to avoid in a computer as data, searching a first dish name in the basic menu table information by the computer in a case where the second information of ingredients to avoid overlaps with the first information of ingredients to avoid by checking the second information of ingredients to avoid in the individual name with the first information of ingredients to avoid in the dish name based on the inputted data, giving a prohibition display to the first dish name when the first dish name exists in a menu region of the basic menu table information, extracting a second dish name having the highest priority in dish names in which the first information of ingredients to avoid does not overlap with the second information of ingredients to avoid in the dish segment where the first dish name to which the prohibition display is given exists, arranging the second dish name having the highest priority in the menu region where the first dish name to which the prohibition display is given exists and outputting individual menu table information corresponding to the individual name.

According to the present invention, the prohibition display is given to the first dish name in each menu region by the computer and the individual menu table information corresponding to the individual name is outputted, therefore, the check error due to work by a human can be eliminated while rationalizing the work. Additionally, it is cleared that the first dish is prohibited by the outputted individual menu table information. Furthermore, it is cleared that the first dish is prohibited and is changed to the second dish by the outputted individual menu table information, which can increase customer satisfaction.

The priorities are set on the side of dining-out places such as a restaurant, a hotel and an inn. As the priorities, for example, the order of good dishes in a dining-out place, the order of dishes having a good reputation for customers, the order of dishes with a plenty of stocks of ingredients in a dining-out place, the order of dishes prices of which are close to a set unit price in a dining-out places and other known priorities are assigned.

The individual menu table information is displayed, for example, on a screen of a display connected to the computer. Moreover, data is transmitted to a portable information terminal data-linked to the computer and is displayed on a screen of a display of the portable information terminal. The individual menu table information is, for example, printed out as a paper medium. According to the above, a person can visually recognize the prohibition display easily.

It is preferable that the prohibition display is strike-through line display on characters and that the second dish name having the highest priority is arranged in a free space close to the strike-through line display on characters. According to the configuration, the prohibition display can be seen at glance, and it is possible to prevent reduction of quality in the prohibition display at the time of outputting the information as the paper medium or the like.

The menu display method may be used, for example, when dishes extracted from a plurality of dish segments are served to a group in a hotel or an inn at meal segments formed by breakfast, lunch and dinner or meal segments formed by time zones, and the user name may be a group name of the group, the first information of ingredients to avoid may be first allergen information and the second information of ingredients to avoid may be second allergen information. According to the configuration, the second dish having the highest priority is served, not a merely substituted dish, to a person having a food allergic disease in a dining-out place, thereby preventing health damage.

A menu display device according to the present invention includes an input means for receiving input of basic menu table information in which menus are associated with a user name and meal segments, dish table information in which dish names forming the menus are respectively associated with dish segments and first information of ingredients to avoid, and priorities are given in the dish segment, and individual table information in which individual names forming the user name are associated with second information of ingredients to avoid as data, a means for searching a first dish name in the basic menu table information in a case where the second information of ingredients to avoid overlaps with the first information of ingredients to avoid by checking the second information of ingredients to avoid in the individual name with the first information of ingredients to avoid in the dish name based on the inputted data, a means for giving a prohibition display to the first dish name when the first dish name exists in a menu region of the basic menu table information, a means for extracting a second dish name having the highest priority in the dish names in which the first information of ingredients to avoid does not overlap with the second information of ingredients to avoid in the dish segment where the first dish name exists in the menu region of the basic menu table information, a means for arranging the second dish name in the menu region in which the prohibition display is given to the first dish name and a means for outputting individual menu table information corresponding to the individual name.

According to the present invention, the work of checking information of ingredients to avoid of dishes in plural menus with information of ingredients to avoid of plural customers is processed by respective means of the menu display device, therefore, the check error due to work by a human can be eliminated while rationalizing the work. Moreover, the work of extracting the second dish name having the highest priority in dish names in which the first information of ingredients to avoid does not overlap with the second ingredients to avoid in the dish segment, the work of displaying the second dish name on each menu region in which the prohibition display is given to the first dish name and the work of outputting individual menu table corresponding to the individual name are processed by respective means of the menu display device, therefore, it is cleared that the first dish is prohibited and changed to the second dish by the outputted individual menu table information, which increases customer satisfaction.

A menu display program according to the present invention allows a computer in which basic menu table information in which menus are associated with a user name and meal segments, dish table information in which dish names forming the menus are respectively associated with dish segments and first information of ingredients to avoid, and priorities are given in the dish segment, and individual table information in which individual names forming the user name are associated with second information of ingredients to avoid are inputted as data to execute a procedure of searching a first dish name in the basic menu table information in a case where the second information of ingredients to avoid overlaps with the first information of ingredients to avoid by checking the second information of ingredients to avoid in the individual name with the first information of ingredients to avoid in the dish name based on the inputted data, a procedure of giving a prohibition display to the first dish name when the first dish name exists in a menu region of the basic menu table information, a procedure of extracting a second dish name having the highest priority in the dish names in which the first information of ingredients to avoid does not overlap with the second information of ingredients to avoid in the dish segment where the first dish name exists in the menu region of the basic menu table information, a procedure of arranging the second dish name in the menu region in which the prohibition display is given to the first dish name and a procedure of outputting individual menu table information corresponding to the individual name.

According to the present invention, the work of giving the prohibition display to the first dish name in each menu region and outputting individual menu table information corresponding to the individual name is executed on the computer by the menu display program, therefore, the check error due to the work by a human can be eliminated while rationalizing the work. Moreover, it is cleared that the first dish is prohibited by the outputted individual menu table information, which increases customer satisfaction.

Advantageous Effects of Invention

According to the present invention, the prohibition display is allowed to be given to the first dish name in each menu region and the individual menu table information corresponding to the individual name is allowed to be outputted by the computer, therefore, the check error due to the work by a human can be eliminated while rationalizing the work. Moreover, it is cleared that the first dish is prohibited by the outputted individual menu table information, which increases customer satisfaction. According to the invention, it is possible to enhance the provision of information with respect to people having food allergic diseases, vegetarians, Muslims, Jews, people having gastrointestinal diseases and so on also in dining-out places, which is highly useful for preventing health damage and so on.

DESCRIPTION OF EMBODIMENTS

Embodiment

Figure 1:
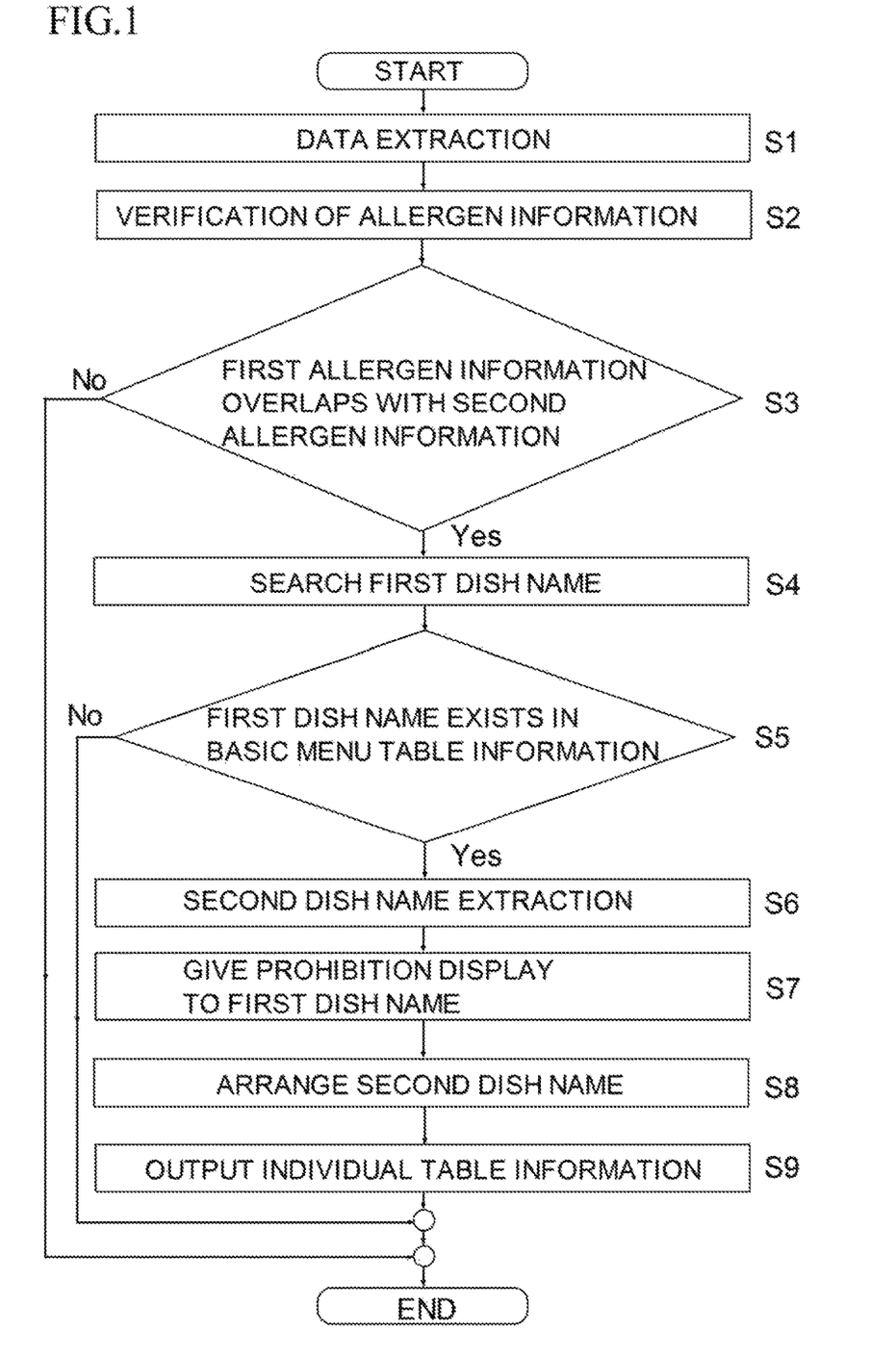
FIG. 1 is a flowchart showing menu display procedures in a menu display method according to an embodiment of the present invention.

Hereinafter, an embodiment of the present invention will be explained in detail with reference to the drawings. The embodiment has a configuration used when dishes are served to people having food allergic diseases in dining-out places. FIG. 1 is a flowchart showing menu display procedures in a menu display method according to the embodiment. In all drawings for explaining the embodiment, the same symbols are given to members having the same functions and repeated explanation thereof may be omitted.

The menu display procedures shown in FIG. 1 include Step S1 of extracting data, Step S2 of checking allergen information. Step S3 of determining whether first allergen information 304 overlaps with second allergen information 404 or not, Step S4 of searching a first dish name 205a when the allergen information overlaps, Step S5 of determining whether the first dish name 205a exists in basic menu table information 20 or not, Step S6 of extracting a second dish name 205b when the first dish name 205a exists, Step S7 of giving a prohibition display 501 to the first dish name 205a, Step S8 of arranging the second dish name 205b close to the first dish name 205a and Step S9 of outputting individual menu table information. The details of the menu display procedures will be described later.

Figure 2:
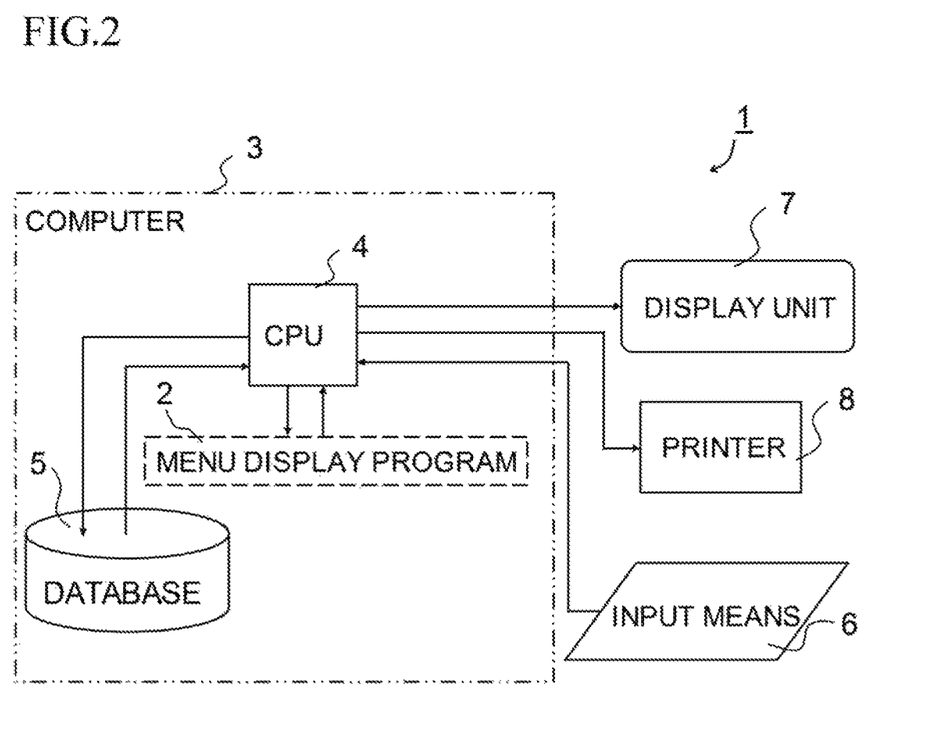
FIG. 2 is a block diagram showing a menu display device according to the embodiment of the present invention in a functional manner.

FIG. 2 is a block diagram showing a menu display device 1 according to the embodiment in a functional manner. The menu display device 1 according to embodiment includes a computer 3 and a menu display program 2 operating on the computer 3. A CPU 4 and a database 5 are installed in the computer 3. Then, a display unit 7, a printer 8 and an input means 6 such as a keyboard and a mouse are connected to the computer 3. The input means 6 may be a touch panel provided on a screen of the display unit 7. As the computer 3, a so-called personal computer for individuals can be adopted.

The menu display program 2 includes a plurality of datasheets displayed on a screen in a table form with plural cell columns and a control program controlling data exchange among these datasheets or data exchange with respect to the data base 5 through the CPU 4.

As an example, the menu display program 2 is stored in a computer readable storage medium such as a USB memory and a CD-ROM. As an example, the menu display program 2 is downloaded to the computer 3 through a network and installed in the computer 3.

As firmware for the menu display program 2 according to the embodiment, EXCEL (registered trademark) of Microsoft Corporation or ACCESS (registered trademark) of Microsoft Corporation can be adopted, and the control program using a macro function included in EXCEL (registered trademark) may be adopted. The control programs using commercially available spreadsheet software and a macro function of the spreadsheet software can be used in addition to the above.

Example

The example will be explained below by citing a case where dishes are served to a group a plural number of times in a hotel, an inn and the like.

Figure 3:
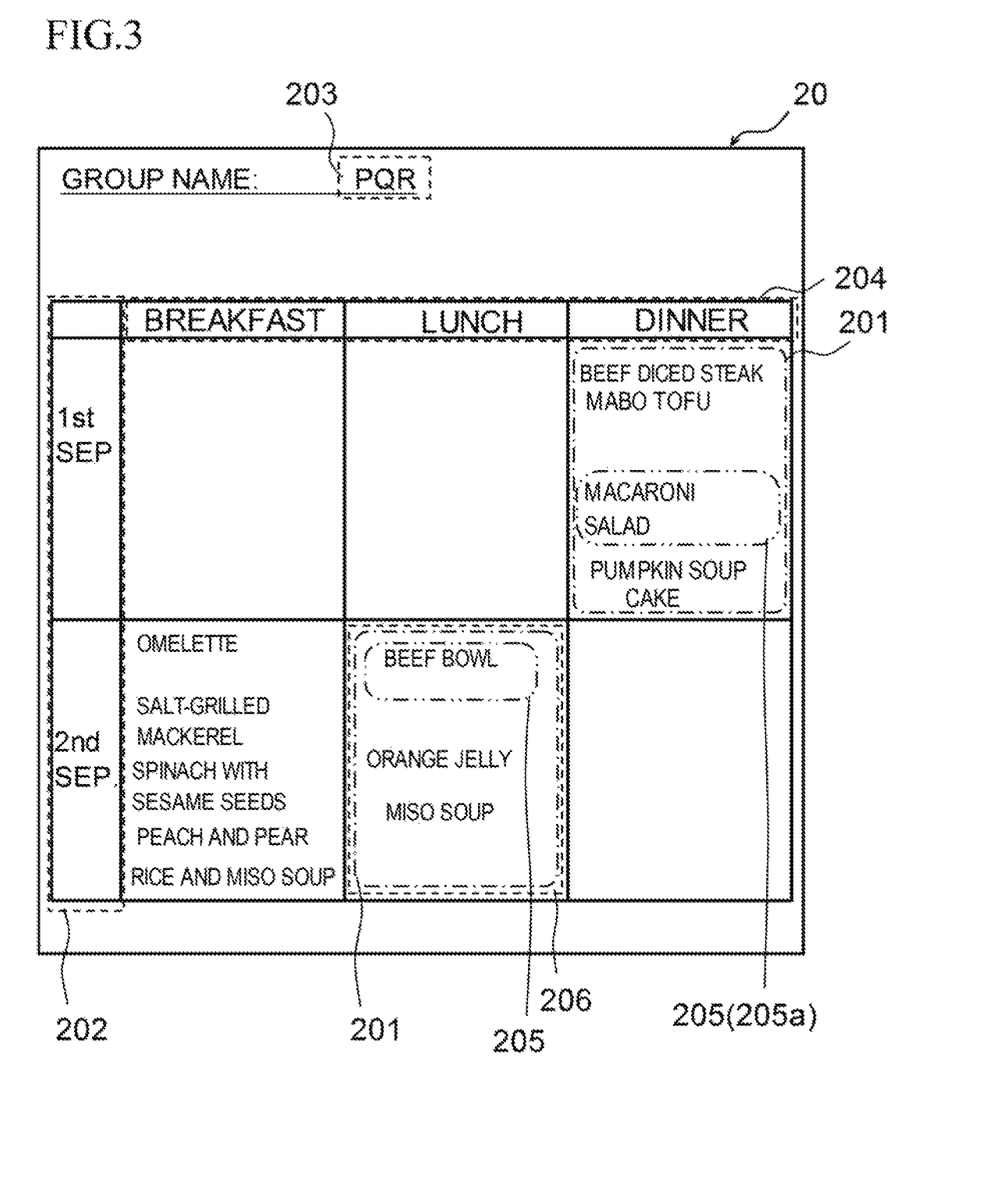
FIG. 3 is a chart illustrating basic menu table information used in the embodiment.
Figure 4:
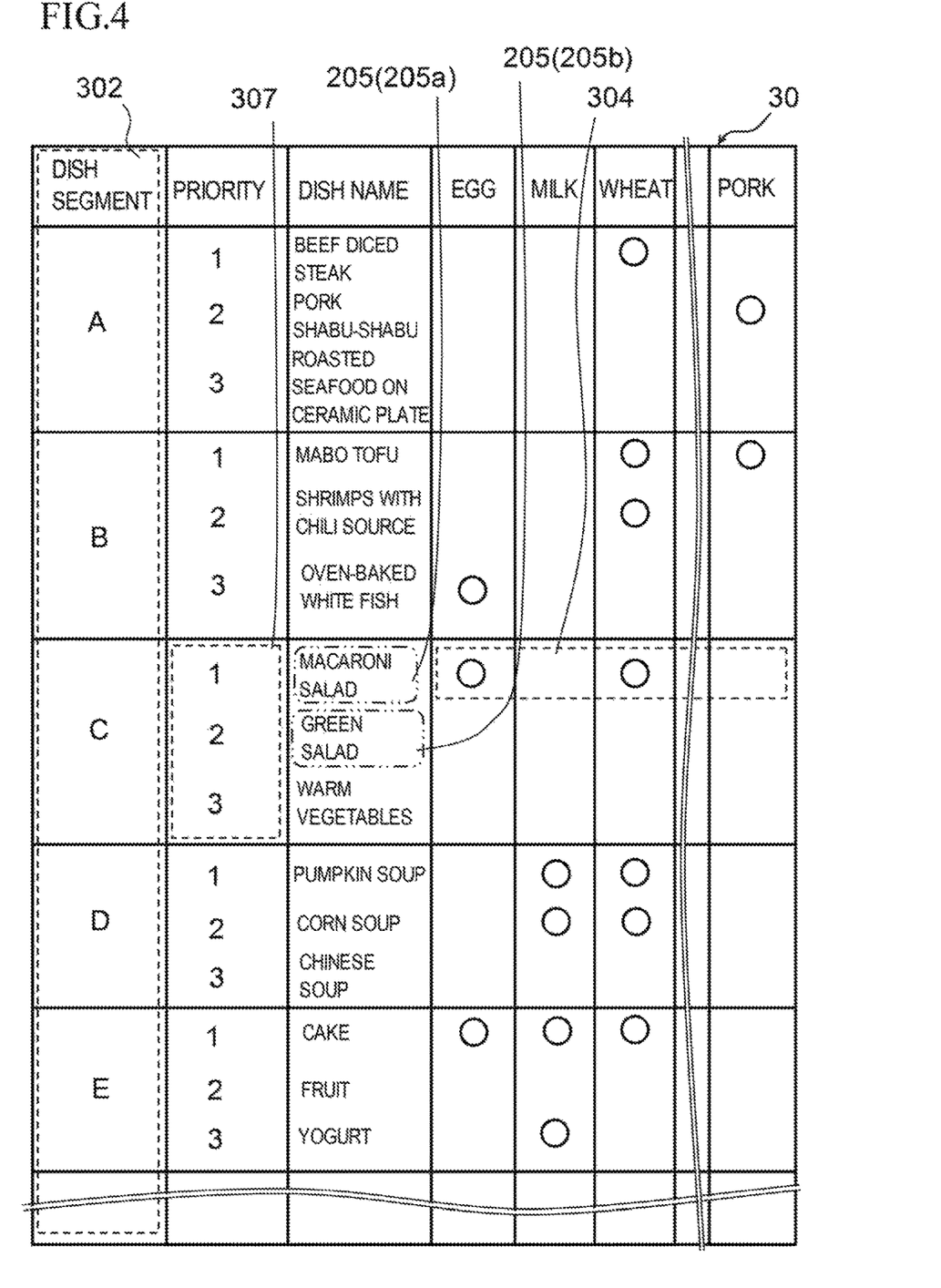
FIG. 4 is a chart illustrating dish table information used in the embodiment.
Figure 5:
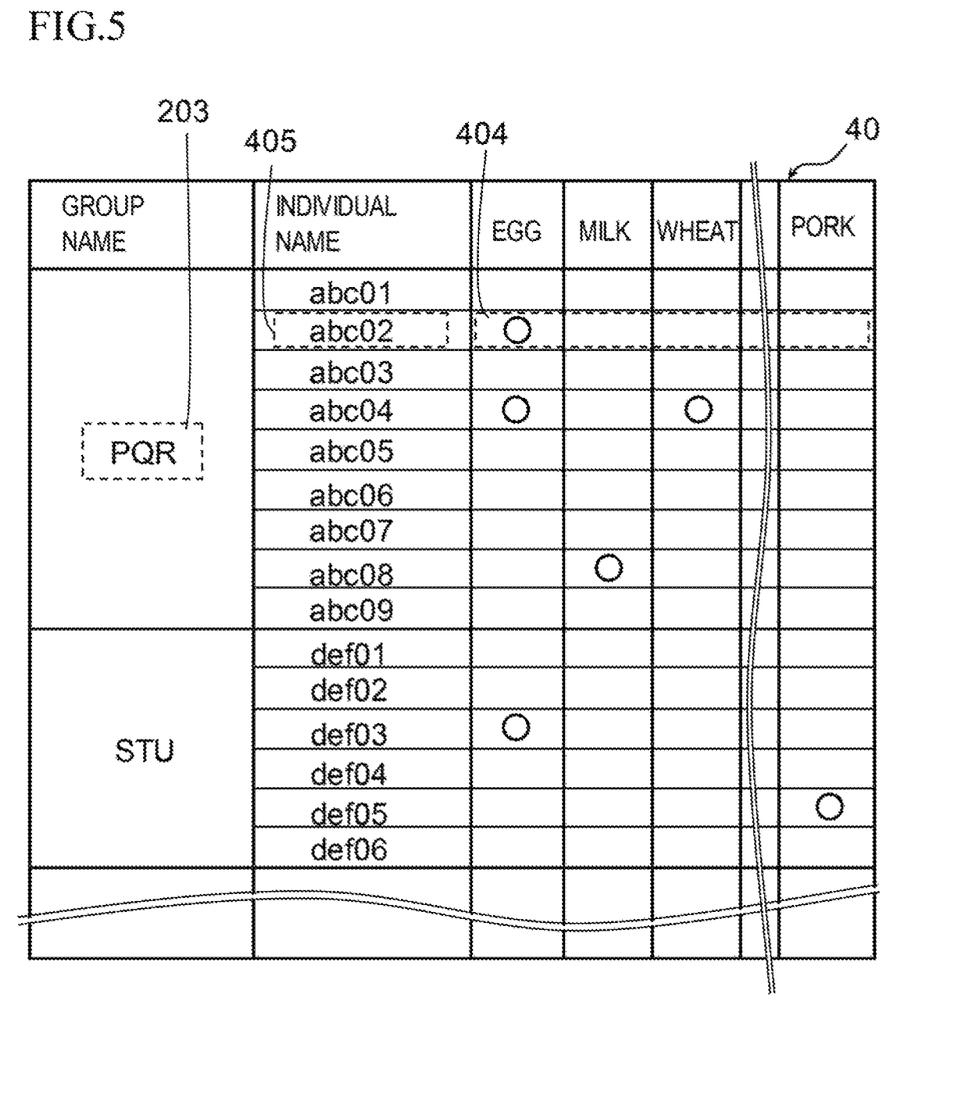
FIG. 5 is a chart illustrating individual table information used in the embodiment.

FIG. 3 is a chart illustrating the basic menu table information 20. FIG. 4 is a chart illustrating dish table information 30 and FIG. 5 is a chart illustrating individual table information 40. As preparation work, the hotel, the inn and the like create the basic menu table information 20, the dish table information 30 and the individual table information 40 based on menu information originally planned by a department in charge of cooking, allergen information obtained from suppliers and so on of ingredients and food, individual allergy information obtained from a representative of the group, a person in charge in a travel agency and the like and other information which can be obtained in advance. As an example, an input screen is displayed on the display unit 7 when the menu display program 2 is started on the computer 3, and data is inputted as instructed by the menu display program 2. A well-known method is adopted as a method of inputting data. As an example, data may be inputted by typing. As an example, there is a case where a paper medium is scanned and captured as data to be inputted.

The basic menu table information 20 shown in FIG. 3 has one-to-one correspondence with a group name 203. A date segment 202 indicates information having one-to-one correspondence with a date such as a month and a day or a date such as a first day or a second day. A meal segment 204 indicates information having one-to-one correspondence with a meal segment such as breakfast, lunch and dinner or a meal segment such as a time zone. A menu region 206 indicates an information region having one-to-one correspondence with each date segment 202 and each meal segment 204. In each menu region 206, a menu 201 is inputted as information or the region is left blank. The menu 201 includes a plurality of dish names 205 or includes at least one dish name 205. The basic menu table information 20 is configured to be displayed on a screen of a computer display as well as configured to be printed out as a paper medium. The date segment 202 is not limited to a case including plural dates but there is a case of a single day.

The dish table information 30 shown in FIG. 4 is information in which the dish names 205 are respectively associated with dish segments 302 and first allergen information 304, and priorities 307 are given in the dish segment 302. The dish segment 302 indicates information having one-to-one correspondence with a dish segment such as a staple food, a main dish, a side dish or a dessert, or a dish segment such as items of a menu. The priorities 307 are set on the side of the hotel or the inn. In the example shown in FIG. 4, the smaller the number is, the higher the priority is. The number of priorities 307 is not limited to three or more, but there is a case where the number thereof is two.

The first allergen information 304 indicates information of specific raw materials and so on to be allergens such as eggs, milk, wheat, peanuts, shrimps, buckwheat, crabs, salmon roe, kiwi fruit, walnuts soybeans, bananas, yams, cashew nuts, peaches, sesame, mackerel, salmon, squid, chicken, apples, matsutake mushroom, abalone, oranges, beef, gelatin, pork and other well-known allergen ingredients. In the example of FIG. 4, allergens corresponding to respective dish names 205 are marked. The invention is not limited to this form, and for example, allergens corresponding to respective dish names 205 may be listed up. The dish table information 30 can be displayed on a screen of the computer display as well as can be printed out as a paper medium.

The individual table information 40 shown in FIG. 5 is information in which individual names 405 are associated with second allergen information 404 respectively in the group name 203. The second allergen information 404 indicates information of specific raw materials and so on to be allergens such as eggs, milk, wheat, peanuts, shrimps, buckwheat, crabs, salmon roe, kiwi fruit, walnuts, soybeans, bananas, yams, cashew nuts, peaches, sesame, mackerel, salmon, squid, chicken, apples, matsutake mushroom, abalone, oranges, beef, gelatin, pork and other well-known allergen ingredients. A format of display and specific raw material names to be displayed are matched in the first allergen information 304 of FIG. 4 and the second allergen information 404 of FIG. 5. According to the above, the first allergen information 304 can be easily checked with the second allergen information 404. The individual information 40 is configured to be displayed on a screen of the computer display as well as configured to be printed out as a paper medium.

When data is inputted as instructed by the menu display program 2 and the preparation work is completed, main work for outputting individual menu table information is performed. Explanation will be made along the menu display procedures shown in FIG. 1.

When the menu display program 2 is started on the computer 3, an input screen is displayed on the display unit 7. An operator inputs the group name 203 as instructed by the menu display program 2, and the computer 3 extracts data (Step S1). The computer 3 checks the second allergen information 404 in the individual name 405 in the individual table information 40 with the first allergen information 304 in the dish name 205 in the dish table information 30 (Step S2). Then, the computer 3 determines whether the first allergen information 304 overlaps with the second allergen information 404 or not (Step S3). As an example, in a case where the individual name 405 is [abc02] and the second allergen information 404 is [egg], it is determined that allergen information overlaps as there is [egg] in [macaroni salad] as the first allergen information 304 in the dish name 205.

Here, there is a case where the second allergen information 404 includes plural allergens in the individual name 405 and there is a case where the first allergen information 304 includes plural allergens in the dish name 205. In such case, it is determined that the first allergen information 304 overlaps with the second allergen information 404 when at least one allergen overlaps, and processing is performed.

Next, when the second allergen information 404 overlaps with the first allergen information 304, the computer 3 searches the first dish name 205a in the basic menu table information 20 (Step S4). Then, the computer 3 determines whether the first dish name 205a exists in the basic menu table information 20 or not (Step S5). As an example, when the first dish name 205a is [macaroni salad], it is determined that [macaroni salad] exists in the basic menu table information 20.

Then, the computer 3 extracts the second dish name 205b having the highest priority 307 in dish names 205 in which the first allergen information 304 does not overlap with the second allergen information 404 in the dish segment 302 in the dish table information 30 (Step S6). As an example, [green salad] is extracted as the second dish name 205b having the highest priority 307 in the dish names 205 in which there is no [egg] in the first allergen information 304.

Here, there is a case where the second allergen information 404 has plural allergens in the individual name 405 and there is a case where the first allergen information 304 has plural allergens in the dish name 205. In such case, it is determined that the first allergen information 304 does not overlap with the second allergen information 404 when any allergen does not overlap, and processing is performed.

Next, the computer 3 gives a prohibition display 501 to the first dish name 205a (Step S7). As an example, [strike-through line display on characters] as the prohibition display 501 is arranged on [macaroni salad] as the first dish name 205a. The prohibition display 501 is any one kind or more of the strike-through line display on characters, a shaded display on characters and red-colored display on characters. According to the display, a person can visually recognize the prohibition display 501.

Here, the processing of giving the prohibition display 501 to the first dish name 205a may be processing of overwriting the first dish name 205a with the prohibition display 501 attached in a corresponding cell. It is also preferable that a multi-layer structure is adopted and that the processing of giving the prohibition display 501 in a second layer on a basic layer in which the first dish name 205a is arranged is adopted. A well-known software technique or a well-known image processing technique is applied to the processing of giving the prohibition display 501 to the first dish name 205a.

Then, the computer 3 arranges the second dish name 205b in the menu region 206 in which the prohibition display 501 is arranged on the first dish name 205a (Step S8). As an example, [green salad] as the second dish name 205b is arranged in a free space close to [macaroni salad] (strike-through line display on characters) as the first dish name 205a in which [strike-through line display on characters] is arranged as the prohibition display 501. As an example, display colors may be changed in a manner in which the first dish name 205a is displayed in red-colored characters and the second dish name 205b is displayed in blue-colored characters or green-colored characters. As an example, a line type is changed in a manner in which a line width of characters of the first dish name 205a is made to be thin, and a line width of the characters of the second dish name 205b is made to be thick. There is no problem that the order of Step S6 and Step S7 is changed and processing is performed in the order of Step S7. Step S6 and Step S8. Moreover, there is no problem that the order of Step S7 and Step S8 is changed and processing is performed in the order of Step S6. Step S8 and Step S7. Step S6 and Step S8 may be omitted.

Figure 6:
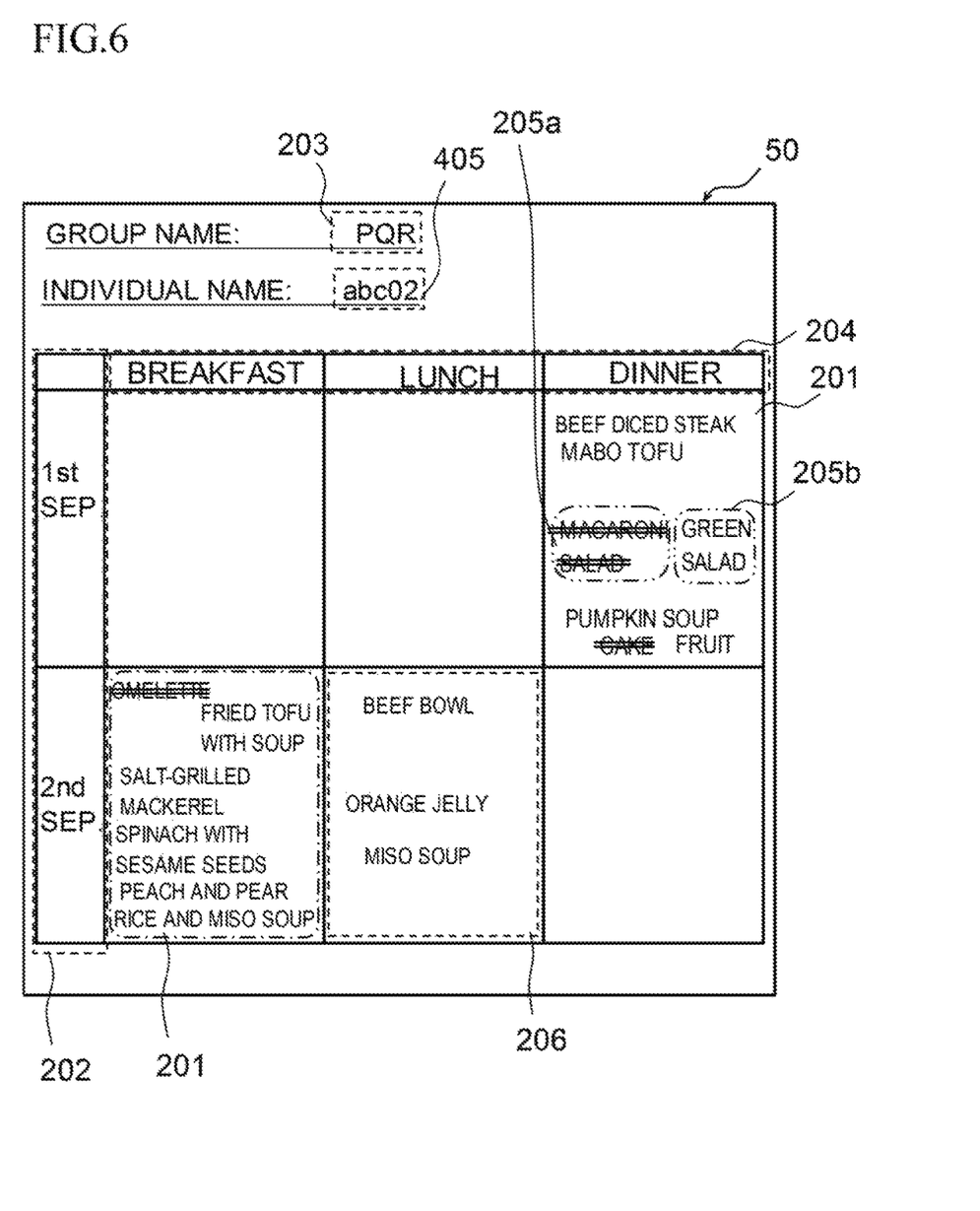
FIG. 6 is a chart illustrating individual menu table information outputted by the embodiment.

Then, the computer 3 outputs the individual menu table information 50 (Step S9). As an example, the individual menu table information 50 is printed out as a paper medium. The individual menu table information 50 is also displayed on a screen of the display unit 7 connected to the computer 3.

According to the embodiment, it is possible to eliminate a check error due to work by a human while rationalizing the work by computer processing. Moreover, it is cleared that the first dish 205a is inhibited by the outputted individual menu table information 50 as well as it is cleared that the first dish 205a is changed to the second dish 205b.

The present invention is not limited to the above embodiment and various modifications may occur in a scope not departing from the present invention. For example, the individual menu table information 50 is displayed on the screen of the display unit 7 connected to the computer 3 in the above explanation, however, the present invention is not limited to the example. For example, there is a case of adopting a structure in which data is transmitted to a portable information terminal data-linked to the computer 3 to be displayed on a screen of a display of the portable information terminal.

For example, there is a case of adopting a structure in which image data of dishes having one-to-one correspondence with the first dish names 205a and the second dish names 205b is arranged respectively to thereby visually recognize appearances of dishes.

The case where dishes are served to people having food allergic diseases in dining-out places is cited as the example in the above embodiment, however, the present invention is not limited to this. When the first allergen information 304 is set as first information of ingredients to avoid and the second allergen information 404 is set as second information of ingredients to avoid, it is possible to cope with cases where respective users of dining-out places such as restaurants, hotels and inns have religious reasons, reasons of diseases and taste in addition to food allergy. Dishes served in dining-out places such as restaurants, hotels and inns can be made of a vegetarian diet, a Muslim diet (halal processed ingredients), a Judaist diet, a gastrointestinal disease diet (digestible ingredients) in addition to an allergen diet.

What is claimed is:
1. A menu display method comprising the steps of:
inputting basic menu table information comprising menus that are associated with a group name of a group of users and meal segments in a computer as data;
inputting dish table information comprising dish names forming the menus in the basic menu table information, wherein the dish names are respectively associated with dish segments and first information of ingredients to avoid, and wherein priorities are given to the dish names with in each dish segment in the computer as data;
inputting individual table information comprising individual names of the group of users, wherein each individual name is associated with second information of ingredients to avoid in the computer as data;
comparing the dish table information with the individual table information for each individual name by checking the second information of ingredients to avoid in the individual name with the first information of ingredients to avoid in the dish name based on the inputted data;
searching a first dish name in the basic menu table information by the computer in a case where the second information of ingredients to avoid overlaps with the first information of ingredients to avoid for a first individual name;
generating an individual menu table information for said first individual name, by
giving a prohibition display to the first dish name when the first dish name exists in a menu region of the basic menu table information;
extracting a second dish name having the highest priority in dish names in which the first information of ingredients to avoid does not overlap with the second information of ingredients to avoid in the dish segment where the first dish name to which the prohibition display is given exists; and
arranging the second dish name having the highest priority in the menu region where the first dish name to which the prohibition display is given exists,
wherein said individual menu table information has the same content in terms of the menus as the basic menu table information except for the prohibition display indicating that the first dish name is being rejected, the prohibition display being a strike-through line display on characters, and the second dish name having the highest priority replacing the first dish name is arranged in a free space close to the strike-through line display on characters, and
wherein the first information of ingredients to avoid is first allergen information and the second information of ingredients to avoid is second allergen information.

2. The menu display method according to claim 1, wherein the method is used when dishes extracted from a plurality of dish segments are served to the group in a hotel or an inn at meal segments formed by breakfast, lunch and dinner or meal segments formed by time zones.

3. A menu display device comprising:
an input means for receiving input of:
basic menu table information comprising menus that are associated with a group name of a group of users and meal segments in a computer as data;
dish table information comprising dish names forming the menus in the basic menu table information, wherein the dish names are respectively associated with dish segments and first information of ingredients to avoid, and wherein priorities are given to the dish names with in each dish segment in the computer as data; and
individual table information comprising individual names of the group of users, wherein each individual name is associated with second information of ingredients to avoid in the computer as data; and
a CPU programmed to:
compare the dish table information with the individual table information for each individual name by checking the second information of ingredients to avoid in the individual name with the first information of ingredients to avoid in the dish name based on the inputted data;
search a first dish name in the basic menu table information by the computer in a case where the second information of ingredients to avoid overlaps with the first information of ingredients to avoid for a first individual name;
generate an individual menu table information for said first individual name, by
giving a prohibition display to the first dish name when the first dish name exists in a menu region of the basic menu table information;
extracting a second dish name having the highest priority in dish names in which the first information of ingredients to avoid does not overlap with the second information of ingredients to avoid in the dish segment where the first dish name to which the prohibition display is given exists; and
arranging the second dish name having the highest priority in the menu region where the first dish name to which the prohibition display is given exists,
wherein said individual menu table information has the same content in terms of the menus as the basic menu table information except for the prohibition display indicating that the first dish name is being rejected, the prohibition display being a strike-through line display on characters, and the second dish name having the highest priority replacing the first dish name is arranged in a free space close to the strike-through line display on characters, and
wherein the first information of ingredients to avoid is first allergen information and the second information of ingredients to avoid is second allergen information.

4. The menu display device according to claim 3, wherein the device is used when dishes extracted from a plurality of dish segments are served to the group in a hotel or an inn at meal segments formed by breakfast, lunch and dinner or meal segments formed by time zones.

5. A non-transitory computer readable medium having recorded therein a computer-implemented menu display program comprising computer-executable program code for, when executed on a computer, instructing the computer to perform the method according to claim 1.

6. The non-transitory computer readable medium according to claim 5, wherein the menu display program is used when dishes extracted from a plurality of dish segments are served to the group in a hotel or an inn at meal segments formed by breakfast, lunch and dinner or meal segments formed by time zones.

* * * * *